United States Patent [19]
Higuchi et al.

[11] B 3,995,635
[45] Dec. 7, 1976

[54] OCULAR INSERT

[75] Inventors: Takeru Higuchi, Lawrence, Kans.;
Anwar A. Hussain, Lexington, Ky.;
John W. Shell, Los Altos, Calif.

[73] Assignee: Alza Corporation, Palo Alto, Calif.

[22] Filed: Nov. 4, 1974

[21] Appl. No.: 520,277

[44] Published under the second Trial Voluntary Protest Program on February 17, 1976 as document No. B 520,277.

Related U.S. Application Data

[63] Continuation-in-part of Ser. No. 179,129, Sept. 9, 1971.

[52] U.S. Cl. .............................. 128/260; 424/15; 424/19
[51] Int. Cl.² ................. A61K 27/12; A61M 31/00
[58] Field of Search ................. 128/260, 261, 156; 424/15, 19–22; 206/.5

[56] References Cited
UNITED STATES PATENTS

| | | | |
|---|---|---|---|
| 3,113,076 | 12/1963 | Jacobs | 424/15 |
| 3,416,530 | 12/1968 | Ness | 128/260 |
| 3,618,604 | 11/1971 | Ness | 128/260 |
| 3,828,777 | 8/1974 | Ness | 128/260 |
| 3,867,519 | 2/1975 | Michaels | 424/19 |

FOREIGN PATENTS OR APPLICATIONS

| | | | |
|---|---|---|---|
| 1,003,914 | 3/1957 | Germany | 128/260 |
| 15,518 | 6/1968 | Japan | 128/260 |

*Primary Examiner*—Aldrich F. Medbery
*Attorney, Agent, or Firm*—Thomas E. Ciotti; Paul L. Sabatine; Edward L. Mandell

[57] ABSTRACT

A drug-dispensing ocular insert containing a drug and suited for application to the eyeball to dispense said drug to the eye over a prolonged period of time, includes, for permitting facile insertion into and comfortable retention within the eye, and more importantly for preventing the accidental expulsion of the insert therefrom, first detent means adapted for insertion into the cul-de-sac of the conjunctiva between the sclera of the eyeball and the upper eyelid, and second, conjoint detent means, cooperative with said first detent means, adapted for insertion into the cul-de-sac of the conjunctiva between the said sclera of the eyeball and the lower eyelid.

13 Claims, 5 Drawing Figures

OCULAR INSERT

CROSS REFERENCE TO RELATED APPLICATION

This application is a continuation-in-part of copending application Ser. No. 179,129, filed Sept. 9, 1971.

BACKGROUND OF THE INVENTION

1. Field of the Invention

The present invention relates to an ocular insert for dispensing drugs to the eye, and, more especially, relates to an ocular insert having an improved size and shape such that the device is easily inserted into and comfortably retained within the eye, but which nevertheless is markedly resistant to expulsion therefrom.

2. Description of the Prior Art

At the present time, diseases of the eye are usually treated by applying ophthalmic drugs in liquid or ointment form. To be effective in many cases, the application of drug should be substantially continuous. Such continuous delivery of drug is not obtained through the use of liquid or ointment dosage forms, even though they be applied at intervals during the day and night. Periodic application of these dosage forms results in the eye receiving a massive, but unpredictable, amount of drug at the time of application, but the drug is washed away rapidly by tears, leaving the eye without medication until the next application. Ointment dosage forms are presently available only in unsterilized form and this too presents a problem.

At a very early time, drugs were dissolved and dispersed in a water-soluble gel of glycerinated gelatin that was shaped to the form of a lamella or eye disk. These lamellae were applied to the inner surface of the eyelid to supply drug to the eye. In use, the glycerinated gelatin vehicle dissolved rapidly to tear liquid, producing the same type of effect as liquid dosage forms. Lamellae were not a sustained-release dosage form. It is understood that same are not used in this country, although they may be used to a small extent in Europe. Further information on these water-soluble dosage forms can be found in Remington's Pharmaceutical Sciences, XIII, pages 547-8 (Mack Publishing Co., Easton, Pa. 1965); Fishburn, An Introduction to Pharmaceutical Formulation, page 116 (Pergamon Press Ltd., New York City, N.Y. 1965); and U.S. Pat. No. 273,410, Mar. 6, 1883.

U.S. Pat. No. 3,416,530, granted Dec. 17, 1968, and assigned to the assignee of this invention, is directed to the invention of a drug-dispensing ocular insert that truly acts as a depot or drug reservoir, retaining the slowly releasing drug to the eye for prolonged periods of time. Such ocular inserts are fabricated of flexible polymeric materials that are biologically inert, nonallergenic, and insoluble in tear liquid. To initiate the therapeutic program, the ocular insert is placed in the cul-de-sac of the conjunctiva between the sclera of the eyeball and the lid. Since the polymeric material from which the ocular insert is formed is insoluble in tear liquid, it retains its integrity and remains intact during the course of therapy, acting as a reservoir to continuously release drug to the eye and surrounding tissues at a rate which is not affected by dissolution or erosion of the polymeric material. On termination of the therapeutic program, the ocular insert is removed from the cul-de-sac. Thus, a single such ocular insert provides the complete ophthalmic dosage regime for a particular time period, on the order of 24 hours or longer. Frequently repeated applications, as is necessary with liquids, ointments, or water-soluble lamellae, often requiring awakening the patient during the night, are avoided.

To provide for release of ophthalmic drug from the polymeric body of the ocular insert, U.S. Pat. No. 3,416,530 describes using polymeric materials which are perforated with capillary openings. While these capillary openings are effective to release drug to the eye, they add considerable complexity to the manufacture of ocular inserts; for it is difficult to control the size of these openings in large-scale manufacturing using various polymers.

An improved drug-dispensing ocular insert, or medication-dispensing tablet for a human eyeball, which even more truly acts as a reservoir for the continuous, prolonged and controlled release of drugs to the eye, and which is not dependent upon the size and number of perforations or pores in the polymeric body of the ocular insert, is described in U.S. Pat. No. 3,618,604, granted Nov. 9, 1971, also assigned to the assignee of this invention. This '604 patented drug-delivery ocular insert to more controlledly deliver drug to the eye over a prolonged period of time, comprises a flexible body of polymeric material insoluble in tear liquid, being non-allergenic and biologically inert, and has an imperforate surface, the said body containing a drug which is dispensed to the eye in a therapeutically effective amount by diffusion through the polymeric material. This ocular insert is adapted for insertion in the cul-de-sac of the conjunctiva between the sclera of the eyeball and either the upper or lower eyelid, to be held in place against the eyeball by the pressure of the lid.

Compare also those drug-dispensing ocular inserts and accessory items therefor described in U.S. Pat. Nos. 3,626,940, 3,630,200, 3,656,481 and 3,710,795.

Nevertheless, certain individual wearers of the aforesaid drug-dispensing ocular inserts, albeit comfortable, and as same are designed to fit under but a single eyelid, have experienced varying difficulties in the regard of maintaining and retaining a given device in proper place under either the upper or lower eyelid while sleeping or during normal ocular motion. In these admittedly rare individuals, certain unspecified normal or abnormal ocular motions during daily wear, or the process known as Bell's Phenomenon while sleeping, whereby the eye has a tendency to roll upward, tend to result in the accidental expulsion of the device from the eye, thus proving annoying and/or depriving the wearer of the beneficial effects of the drug entity contained therein.

SUMMARY OF THE INVENTION

Accordingly, it is a primary object of this invention to provide an improved drug-dispensing ocular insert of a size and shape adapted for easy insertion into and comfortable retention within the eye, but which is concomitantly more resistant to expulsion therefrom.

Another object of the invention is to provide an improved drug-dispensing ocular insert which is comfortable to wear for long periods of time, and which is neither easily expelled from nor causes discomfort to the eye during sleeping and normal daily wear.

In attaining the objects of the present invention, one feature resides in a drug-dispensing ocular insert fabricated of a size and shape comprising a plurality of detent members, at least one of which being adapted for insertion in the direction of the superior fornix in the conjunctival sac of the conjunctiva between the sclera of the eyeball and the upper eyelid, and at least one of which being adapted for insertion in the direction of the inferior fornix in the conjunctival sac of the conjunctiva between the said sclera of the eyeball and the lower eyelid. The normal pressures of the said upper and lower eyelids serve to maintain and retain the subject ocular insert in place, and the drug released by the device is transported to the eye and surrounding tissue by the flow of tear liquid and by the blinking action of the eyelids.

Other, specific features of the invention reside in [1] an ocular insert comprising a relatively thin, flattened annular ring adapted to be disposed about the eyeball in a position completely posterior of the sulcus sclerae, and wherein at least one portion of the band defining the annulus, ring or toroid provides the detent member for insertion to the vicinity of the superior fornix and at least one other portion of said band provides the detent member for insertion to the vicinity of the inferior fornix, and [2] an ocular insert comprising a relatively thin, flattened horseshoe, crescent, sickle, lune, semicircle, semitoroid, arcuate or other "bifurcated" element, also adapted to be placed about the eyeball in a position completely posterior of the sulcus sclerae, and here wherein at least one of the horns defining the bifurcated insert provides the superior fornix detent member, and at least another horn defines the inferior fornix detent member.

Other objects, features and advantages of this invention will become more apparent from the following description, when taken in conjunction with the accompanying drawings, and wherein like reference numerals are used to indicate like or equivalent parts.

DETAILED DESCRIPTION OF THE INVENTION

Figure 1:
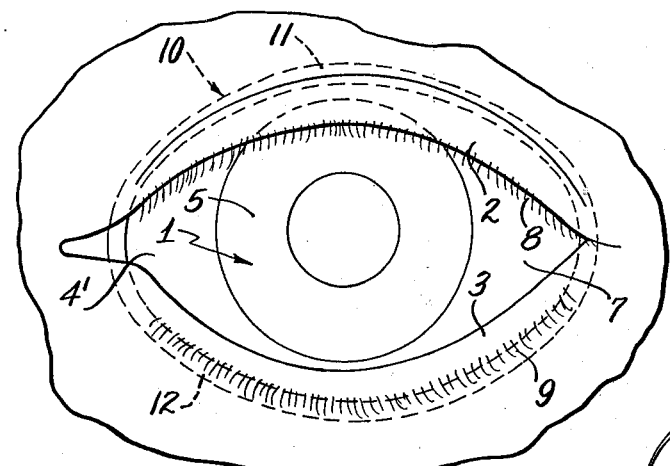
FIG. 1 is a view partly in front elevation and partly diagrammatic, of a human eye, illustrating the use of one ocular insert according to the invention.
Figure 2:
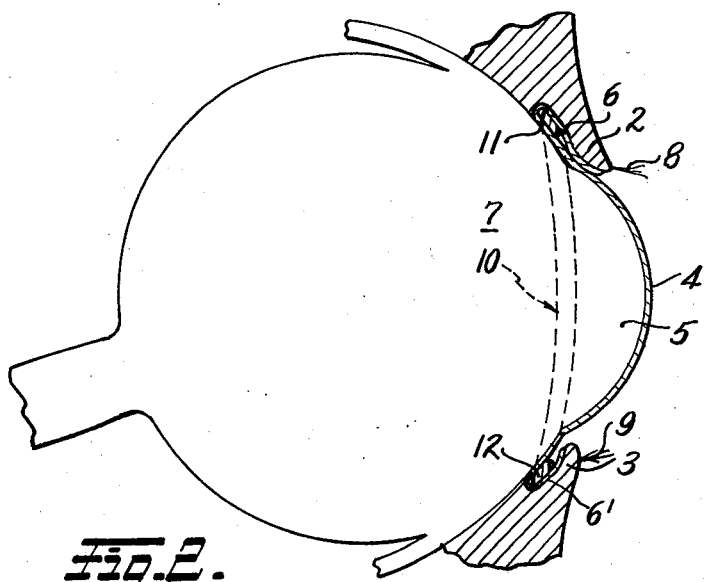
FIG. 2 is a view partly in vertical section and partly diagrammatic of an eyeball and the upper and lower eyelids associated therewith, depicting the placement of the ocular inserts according to the invention.
Figure 4:
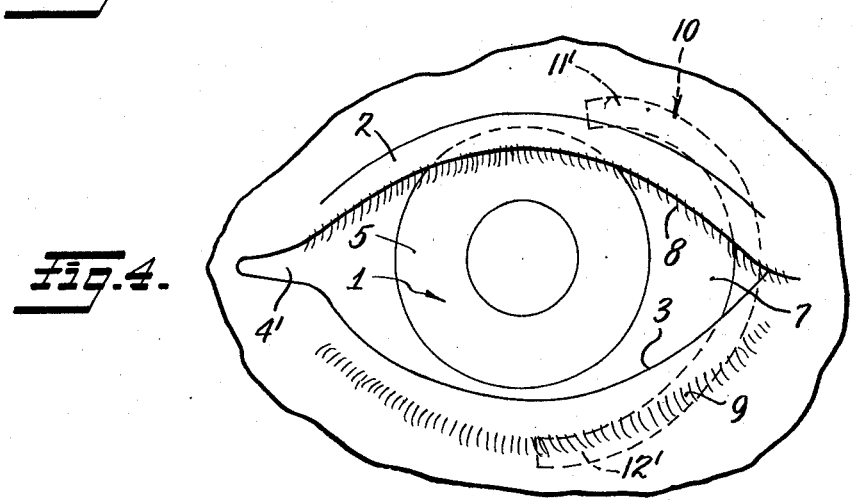
FIG. 4 is a view partly in front elevation and partly diagrammatic of a human eye, illustrating the use of another ocular insert according to the invention.

With specific reference to the FIGS. 1, 2 and 4, a human eye is depicted, more or less diagrammatically, as comprising an almost spherical ocular bulbus or eyeball 1, and upper and lower eyelids 2 and 3, respectively, consisting of loose movable folds of integument protecting the front of the eye. These eyelids 2 and 3 overlap the part of the eyeball that projects beyond the orbit; that space between the free margins of the said eyelids being designated the palpebral fissure. This is a mere slit when the lids are closed, but when they are open its shape is much like that of an almond, some 30 mm. long. Medial and lateral angles, or canthi, are formed by the meeting of the lids at each end of the palpebral aperture, while the unions themselves constitute the corresponding palpebral commissures. At the free margins of the eyelids 2 and 3, the skin assumes the characteristics of a mucous membrane that lines the inner surfaces of the said lids as the palpebral conjunctiva 4. This mucosal lining is then reflected back upon itself at the base of each eyelid where the arching folds are designated, respectively, the superior and inferior fornix. Continuing over the surface of the eyeball 1 as the bulbar conjunctiva 4' as far as the edge of the cornea 5, its epithelium alone [the corneal epithelium] is carried across the transparent front of the eye. There is thus formed a conjunctival sac or cul-de-sac 6 whose anterior wall is supplied by the inner surfaces of the two eyelids 2 and 3 and whose posterior wall lies upon the front third of the eyeball. The anterior, clear front [the cornea 5] of the eyeball bulges beyond the curvature of the larger, white remainder [the sclera 7], and the said sclera 7 behind the cornea 5 in front are joined at the sulcus sclerae. Upper and lower eyelashes are indicated at 8 and 9, respectively. Other details of the structure of the eye are not directly concerned with the improved structure of the instant invention, detailed showing and description thereof being therefore omitted for the sake of brevity. Reference is made, however, to Morris', Human Anatomy, pages 1,221–1,263, 11th Edition, McGraw-Hill (1953).

Figure 3:
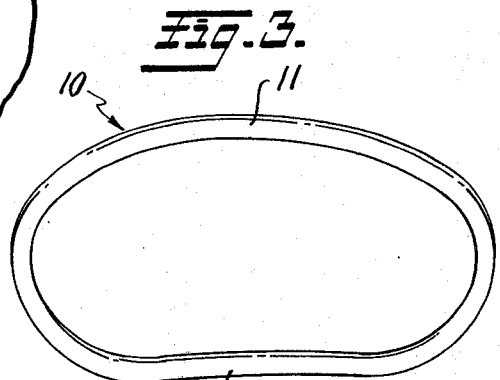
FIG. 3 is a plan view of the one preferred ocular insert of this invention.

In one preferred embodiment in accordance with this invention, as illustrated in FIGS. 1, 2 and 3, a band defining a toroidal or annular drug-dispensing ocular insert 10 [shown by dash lines in FIG. 1] is placed about the entire scleral or non-corneal circumference of the eyeball 1. The upper marginal edge portion of the band of the ocular insert 10 defines first detent means 11 and is placed in the conjunctival sac or cul-de-sac 6 of the conjunctiva 4 between the sclera 7 of the ocular bulbus 1 and the upper eyelid 2. The lower marginal edge portion of the band of the ocular insert 10 defines second, conjoint detent means 12, functionally cooperative with said first detent means 11 to retain and maintain the device 1 in place, and is placed in the conjunctival sac or cul-de-sac 6' of the conjunctiva 4 between the sclera 7 of the ocular bulbus 1 and the lower eyelid 3. Most preferably, this drug-dispensing ocular insert 10 is marginally or peripherally elliptical in shape and is rounded or bowed to conform to the configuration of the scleral curvature [see FIG. 3]. Thus, the drug-dispensing ocular insert 10 shown in FIG. 3 is well adapted for facile insertion into and comfortable retention within the eye, and concomitantly is markedly resistant to expulsion therefrom. The natural pressures of both upper eyelid 2 and lower eyelid 3 against the said first detent means 11 and said second detent means 12, respectively, cooperate to maintain the said ocular insert 10 in place. The lateral ends of said ocular insert 10 are, moreover, fabricated in a shape adapted for placement closely contiguous their respective palpebral commissures, and are, externally, virtually invisible, or are at least totally unobtrusive to the observer.

Figure 5:
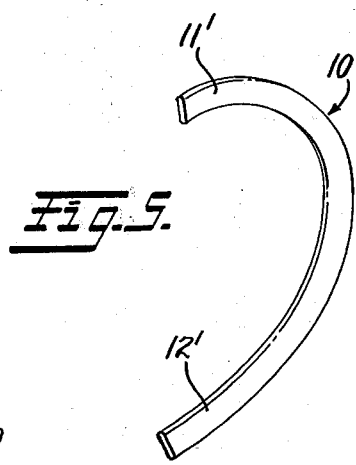
FIG. 5 is a plan view of the another preferred ocular insert of this invention.

In another preferred embodiment in accordance with this invention, as illustrated in FIGS. 4 and 5, and which would similarly be shown as in the FIG. 2, a horseshoe-, crescent-, sickle-, semitoroidal- or semicircular-shaped [hereinafter and in the claims, "lunular" in shape] ocular insert 10 [shown in dash lines in FIG. 4] is placed about only a portion of the scleral or non-corneal circumference of the eyeball 1. One arm or horn, hereby designated the upper arm or horn, of the said ocular insert 10, defines first detent means 11' and is placed in the conjunctival sac or cul-de-sac 6 of the conjunctiva 4 between the sclera 7 of the ocular bulbus 1 and the upper eyelid 2. The other or lower arm or horn of the device 10 defines second, conjoint detent means 12', functionally cooperative with said first detent means 11' to retain and maintain the device in place, and is placed in the conjunctival sac or cul-de-sac 6' of the conjunctiva 4 between the sclera 7 of the ocular bulbus and the lower eyelid 3. Most preferably, this particular drug-dispending ocular insert 10 is semi-elliptical in shape and is rounded or bowed to conform to the configuration of the scleral curvature [see FIG. 5]. Thus, the drug-dispensing ocular insert 10 shown in the FIG. 5 is also well adapted for facile insertion into and comfortable retention within the eye, and concomitantly too is markedly resistant to expulsion therefrom. Again, the natural pressures of both upper eyelid 2 and lower eyelid 3 against the superior horn detent means 11' and the inferior horn detent means 12', respectively, maintain the said ocular insert 10 in place. The medial region of said ocular insert 10, moreover, is also fabricated in a shape adapted for placement closely contiguous either the medial or lateral palpebral commissure, depending upon the intended orientation of the device, and is likewise externally, virtually invisible, or is at least totally unobtrusive to the observer.

With any ocular insert according to the invention firmly entrapped under and by means of the cooperative pressure of both lids 2 and 3, such device is comfortable to the wearer, markedly resistant to expulsion from the eye and does not contact the cornea during sleeping nor during normal ocular motion. Once in place, the ocular insert 10 functions as a drug reservoir gradually releasing drug to the eye and surrounding tissue. Drug released from the ocular insert is transported to the eyeball 1 by the flow of tear liquid and by the blinking action of the eyelids. By use of the ocular insert, the eye is continuously bathed with drug over a particular time span. Normally, the ocular insert 10 will be retained in place for a period of 24 hours, thereby supplying the complete dosage regime for eye therapy over that period of time.

The ocular insert, most advantageously non-allergenic, non-irritating and biologically inert, can be fabricated in any convenient shape permitting simultaneous, comfortable retention in each of the cul-de-sacs. It is most advantageous, however, that the unit device as well as the plurality of conjoint detent means comprising the same individually and jointly have no sharp, jagged, or rough edges which can irritate the sensitive tissues of the eye. Thus, the gross marginal outline of the ocular insert can be circular, elliptical, bean-shaped, rectangular, horseshoe-shaped, doughnut-shaped, semicircular, arcuate, sickle-shaped, crescent-shaped, banana-shaped, or "lunular" and the like. In cross-section, the device can be concavo-convex, elliptical, doubly convex, rectangular, and the like. As the ocular insert is most preferably flexible and, in use, will assume essentially the configuration of the scleral curvature, the original shape of the device is not of controlling importance. It is preferred, though, that the device initially be adapted to conform to the scleral curvature. The device must be of a manipulatable and functional size, namely, must be of a size large enough to permit its manual placement in the both cul-de-sacs. In the case of a FIG. 3 type continuous device, the "ring", usually an elliptical, flattened toroidal member, must be large enough that the band defining the same can extend into each cul-de-sac to the vicinity of the fornix, and the band should additionally traverse a lateral expanse to such extent that the side marginal edges thereof come closely contiguous the respective palpebral commissures. The width of the "band" defining any FIG. 3 device, moreover, should be such that the insert is virtually invisible in the palpebral fissure when the eyelids are open. Similarly, in a FIG. 5 type device, usually horseshoe-shaped, the horns or arms must each be of a length to reach to the vicinity of the fornix of each respective conjunctival sac; likewise its curvature and width are such that it too is virtually invisible when viewed through the palpebral fissure. Actual dimensions of the insert can vary widely. The lower limit on the size of the device is governed by the amount of the particular drug to be applied to the eye and surrounding tissue to elicit the desired pharmacological response, as well as by the smallest sized device which can conveniently be inserted and removed from the eye, while at the same time satisfying the foregoing specifications of functional geometry and virtual invisibility. The upper limit on the size of the insert is governed by the gross space limitations in the eye, consistent with comfortable retention and also at the same time satisfying the specifications of functional geometry and virtual invisibility. Satisfactory FIG. 3 type devices are up to and even in excess of about 25 to 35 mm. in overall length, up to and even in excess of about 18 to 28 mm. in overall height; the band is about 1 to 12 mm. in width, and about 0.1 to 2 mm. in thickness. Preferably, the FIG. 3 device is an ellipsoidal, flattened annular ring, adapted to conform to the scleral curvature, 27 to 33 mm. laterally, 20 to 27 mm. vertically, 2 to 8 mm. in width and 0.1 to 1.5 mm. in thickness. A satisfactory FIG. 5 type device would have dimensions akin to the above, except that its corresponding lateral or horizontal extent would desirably be in the range, 5 to 20 mm.

No matter what the size and shape of the ocular insert according to the invention, it can be functionally constructed as to be of the depot or drug reservoir capillary type disclosed in the U.S. Pat. No. 3,416,530, or the polymeric body diffusion type of U.S. Pat. No. 3,618,604, of U.S. Pat. No. 3,630,200 and of U.S. Pat. No. 3,710,795, or even of the bioerodible type of German Offen. No. P2243986, published Mar. 29, 1973, or of any other type for that matter. The immediately aforesaid patents and publications are hereby expressly incorporated by reference and relied upon for complete disclosure of, inter alia, the various fabrication techniques for the various functional genera, for description of the various polymeric and other systems comprising the same, and the like.

Any of the drugs used to treat the eye and surrounding tissues can be incorporated in the ocular insert of this invention. Also, it is practical to use the eye and surrounding tissues as a point of entry for systemic drugs that enter circulation in the blood stream and produce a pharmacologic response at a site remote from the point of application of the ocular insert. Thus, drugs which will pass through the eye or the tissue surrounding the eye to the bloodstream, but which are not used in therapy of the eye itself, can be incorporated in the ocular insert.

Suitable drugs for use in therapy of the eye with the ocular insert include, without limitation: Anti-infectives: such as antibiotics, including tetracycline, chlortetracycleine, bactracin, neomycin, polymyxin, gramicidin, oxytetracycline, chloramphenicol, and erythromycin; sulfonamides, including sulfacetamide, sulfamethizole, sulfisoxazole; antivirals, including idoxuridine; and other anti-infectives including nitrofurazone and sodium propionate; Antiallergenics such as antazoline, methapyrilene, chlorpheniramine, pyrilamine and prophenpyridamine; Anti-inflammatories such as hydrocortisone, hydrocortisone acetate, dexamethasone, dexamethasone 21-phosphate, fluocinolone, medrysone, prednisolone, prednisolone 21-phosphate and prednisolone acetate; Decongestants such as phenylephrine, naphazoline, and tetrahydrazoline; Miotics and anticholinesterases such as pilocarpine, eserine salicylate, carbachol, diisopropyl flurophosphate, phospholine iodide, and demecarium bromide; Mydriatics such as atropine sulfate, cyclopentolate, homatropine, scopolamine, tropicamide, eucatropine, and hydroxyamphetamine and Sypathomimetics such as epinephrine. Drugs can be in various forms, such as uncharged molecules, components of molecular complexes, or nonirritating, pharmacologically acceptable salts, such as borate, acetate, maleate, tartrate, salicylate, etc. Furthermore, simple derivatives of the drugs (such as esters, ethers, amides, etc.), which have considerable retention and release characteristics but which are easily hydrolyzed by body pH, enzymes, etc. can be employed. The amount of drug incorporated in the ocular insert varies widely, depending on the particular drug, the desired therapeutic effect, and the time span for which the ocular insert will be used. Since the ocular insert is intended to provide the complete dosage regime for eye therapy for but a particular time span, such as 24 hours, there is no critical upper limit on the amount of drug incorporated in the device. For when the device is removed and disposed of it makes little difference whether any drug remains in the device. The lower limit will depend on the activity of the drug and its capability of being released from the device. Thus it is not practical to define a range for the therapeutically effective amount of drug incorporated into the device. However, typically, from 1 microgram to 1 milligram of drug is incorporated in the ocular insert.

While there have been described and pointed out the fundamental novel features of the invention as applied to the preferred embodiments, those skilled in the art will appreciate that various modifications, changes, and omissions in the ocular insert illustrated and described can be made without departing from the spirit of the invention. It is the intention, therefore, to be limited only by the scope of the following claims.

What is claimed is:

1. In a non-corneal, drug dispensing ocular insert comprising a flexible body containing a drug for application to the eyeball to dispense said drug to the eye over a prolonged period of time, the improvement comprising a means for permitting facile insertion into and comfortable retention within the eye, and concomitantly preventing the expulsion of the insert therefrom, wherein said flexible body comprises an annular ring that is sized relative to the eye so it can be placed about the eyeball and in contact therewith, completely posterior to the sulcus sclerae and within the upper and lower cul de sacs, the width of the ring being such that the ring is virtually invisible in the palpebral fissure when the eyelids are open.

2. The ocular insert as defined by claim 1, wherein the annular ring is peripherally elliptical in shape, and is thin and flattened.

3. The ocular insert as defined by claim 2, wherein the annular ring is bowed to the configuration of the scleral curvature.

4. The ocular insert as defined in claim 2 wherein said width is 2 to 8 mm.

5. The ocular insert as defined by claim 1, containing an ophthalmic drug.

6. The ocular insert as defined by claim 1, containing a systemically active drug which will pass through the eye to the bloodstream and elicit a pharmacologic response at a site remote from the eye.

7. The ocular insert as defined in claim 1 wherein said width is about 1 to 12 mm.

8. In a non-corneal, drug dispensing ocular insert comprising a flexible body containing a drug for application to the eyeball to dispense said drug to the eye over a prolonged period of time, the improvement for permitting facile insertion into and comfortable retention within the eye, and concomitantly preventing the expulsion of the insert therefrom, wherein the said flexible body comprises a lunular ring that is sized relative to the eye so it can be placed partly about the eyeball and in contact therewith, completely posterior to the sulcus sclerae and within the upper and lower cul de sacs, the width of the ring being such that the ring is virtually invisible in the palpebral fissure when the eyelids are open.

9. The ocular insert as defined in claim 8 wherein said width is about 1 to 12 mm.

10. The ocular insert as defined in claim 8 wherein said width is about 2 to 8 mm.

11. The ocular insert as defined in claim 8, containing an ophthalmic drug.

12. The ocular insert as defined in claim 8, containing a systemically active drug which will pass through the eye to the bloodstream and elicit a pharmacologic response at a site remote from the eye.

13. The ocular insert as defined by claim 8, wherein the lunular ring is bowed to the configuration of the scleral curvature.

* * * * *